United States Patent [19]

Barber

[11] 4,070,707
[45] Jan. 24, 1978

[54] REDUCTION OF OFFSETS IN DATA ACQUISITION SYSTEMS

[75] Inventor: William D. Barber, Ballston Lake, N.Y.

[73] Assignee: General Electric Co., Schenectady, N.Y.

[21] Appl. No.: 704,413

[22] Filed: July 12, 1976

[51] Int. Cl.² .................. H03K 13/02; G01N 23/00
[52] U.S. Cl. ............................. 364/414; 364/515; 250/445 T; 340/347 CC
[58] Field of Search ................ 250/445 T; 328/127, 328/162; 235/151.3

[56] References Cited

U.S. PATENT DOCUMENTS

| | | | |
|---|---|---|---|
| 3,541,320 | 11/1970 | Beall | 235/183 |
| 3,667,055 | 5/1972 | Uchida | 328/127 |
| 3,879,668 | 4/1975 | Edwards | 328/145 |
| 3,893,103 | 7/1975 | Prill | 340/347 CC |
| 3,940,625 | 2/1976 | Hounsfield | 250/490 X |
| 3,973,128 | 8/1976 | LeMay | 250/445 T |
| 3,996,467 | 12/1976 | Froggatt et al. | 250/445 T X |
| 4,002,911 | 1/1977 | Hounsfield | 250/445 T X |
| 4,008,400 | 2/1977 | Brunnett et al. | 250/445 T |

*Primary Examiner*—Edward J. Wise
*Attorney, Agent, or Firm*—Lawrence D. Cutter; Joseph T. Cohen; Jerome C. Squillaro

[57] ABSTRACT

A data acquisition system, for use in computerized x-ray tomography equipment, comprises hundred data transmission channels, each of which includes a ramp comparison type (i.e., a single slope) A/D converter. The comparator elements in the converters may exhibit substantial propagation delays which contribute to offsets in the values of data transmitted through the channels.

The effect of comparator propagation delays may be reduced by preconditioning each converter before each digitization: a small signal voltage is injected into each converter. The injected voltage is then removed by a linear integration which is terminated in response to an output signal from the comparator element. A negative residue voltage remains on each converter circuit which, during a subsequent digitization, functions to cancel the offsets produced by propagation delays in that circuit.

10 Claims, 16 Drawing Figures

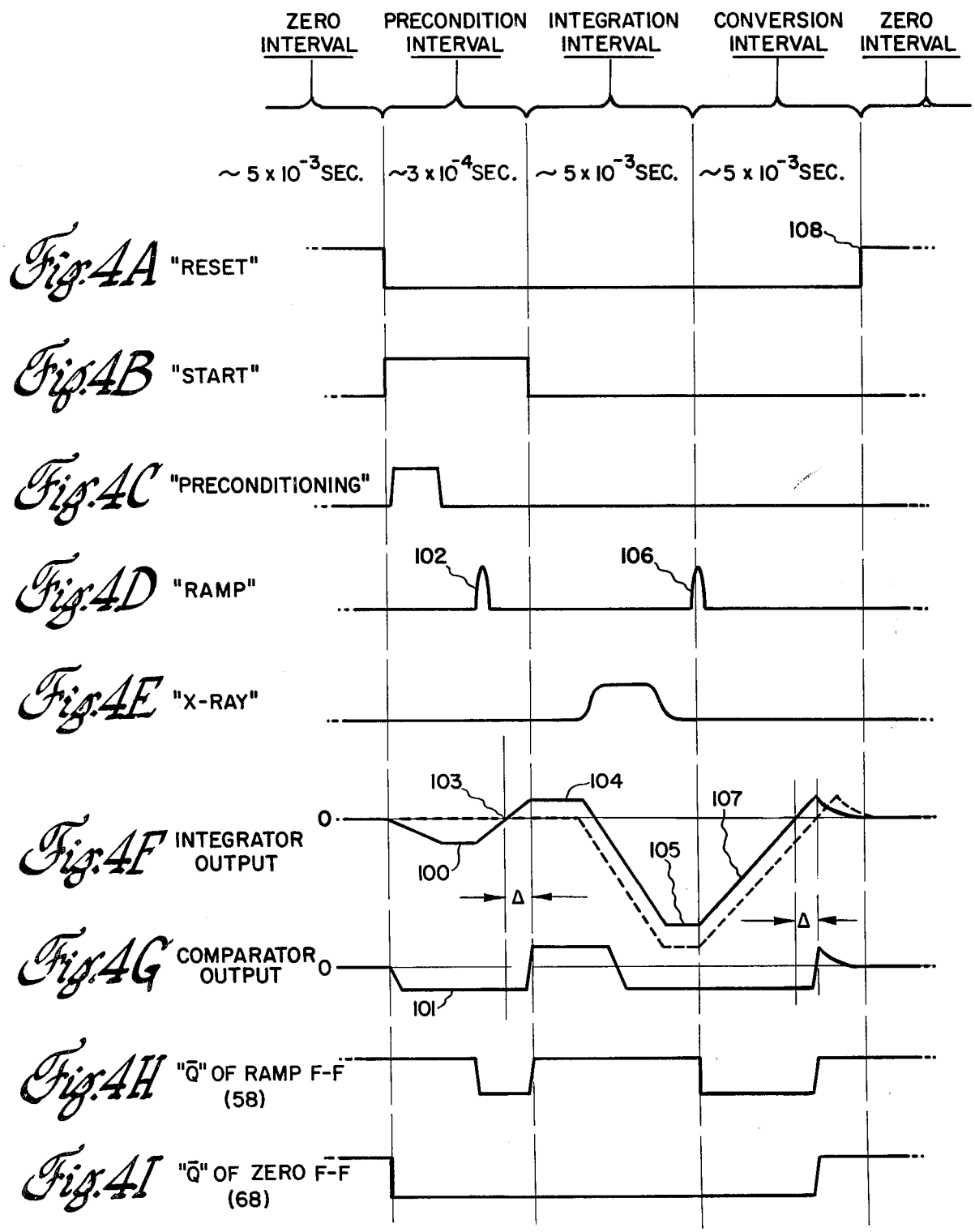

REDUCTION OF OFFSETS IN DATA ACQUISITION SYSTEMS

BACKGROUND OF THE INVENTION

This invention relates to multi-channel x-ray data acquisition equipment for use in computerized transverse axial tomography systems. More specifically, this invention relates to electronic circuits for acquiring and digitizing x-ray transmission data along a plurality of ray paths and to circuits and methods for calibrating such equipment and for compensating the data for drift in channel gain and dc offset parameters.

Shadow-free images of internal body structures may be produced by the methods of computerized transverse axial tomography. In a typical application of those methods, a moving x-ray source is repeatedly pulsed to transmit x-ray energy along a plurality of distinct ray paths through a body undergoing examination. Energy transmitted through the body is detected in an array of x-ray sensors and interpreted, typically by use of a digital computer, to produce x-ray images of internal body sections. The methods of computerized tomography are more specifically described, for example, in U.S. Pat. No. 3,778,614 to Hounsfield which is incorporated in this disclosure, by reference, as background material.

Modern tomography equipment typically comprises arrays of hundreds of X-ray sensors (for example, ionization chambers) which function to simultaneously measure x-ray transmission over a large number of ray paths. Information from each sensor typically must be amplified, conditioned, and digitized to permit the calculation and generation of image data in a digital computer. During a typical tomographic examination, the x-ray source and sensor array rotate and/or translate about the body to acquire data from hundreds of x-ray projections in a few seconds. X-ray data from each sensor must be transmitted to the computer with an accuracy on the order of one part in $2^{14}$ or more to permit the production of high resolution images. The electronic gain and voltage offset in each of the hundreds of data channels are, however, subject to drift; for example, under conditions of temperature change or mechanical motion. It is, therefore, necessary to continuously and automatically calibrate each data acquisition channel during a tomographic examination procedure.

SUMMARY OF THE INVENTION

In accordance with the present invention, a tomographic imaging system comprises a pulsed x-ray source disposed opposite a sensor array which includes hundreds of ionization chamber x-ray detectors. Each ionization chamber in the array drives a data acquisition channel which comprises a buffer amplifier, an integrator, and an analog-to-digital converter. A negative feedback loop, which functions in the interval between x-ray pulses, acts to establish a zero effective current level at the input of the integrator. A single amplifier element functions both as the comparator of the analog-to-digital converter and as a gain element in the feedback loop.

The comparator element must operate as a substantially linear element to assure stable operation of the feedback loop. Comparator elements of this type may, however, exhibit substantial propagation delay times. These delays will produce offsets in the output signals which may differ substantially between channels.

A preconditioning circuit is provided which functions to produce a negative residue signal in each analog-to-digital converter which is proportional to the propagation delay of the associated comparator element. Each residue signal is, then, effectively subtracted from an ionization chamber signal to cancel the offsets of the channel.

All of the data acquisition channels share common bias voltages, reference voltages, calibration signals, clock signals, and timing signals. Errors which might be caused by drift of these signals and voltage among the channels is thereby eliminated.

It is, therefore, an object of this invention to provide circuits and methods for calibrating and stabilizing the transfer function of data acquisition channels in x-ray tomography equipment.

Another object of this invention is to provide circuits for the automatic calibration and compensation of x-ray transmission data in tomography systems.

Another object of this invention is to provide simple, yet highly stable, integrator and analog-to-digital converter circuits for use in data acquisition equipment.

BRIEF DESCRIPTION OF THE DRAWINGS

The novel features believed characteristic of the present invention are set forth in the appended claims. The invention itself, together with further objects and advantages thereof, may best be understood by reference to the following detailed description taken in connection with the appended drawings in which:

FIGS. 4A–4I are waveforms associated with the data acquisition channels of FIG. 2;

DESCRIPTION OF THE PREFERRED EMBODIMENTS

The Data Acquisition System

Figure 1:
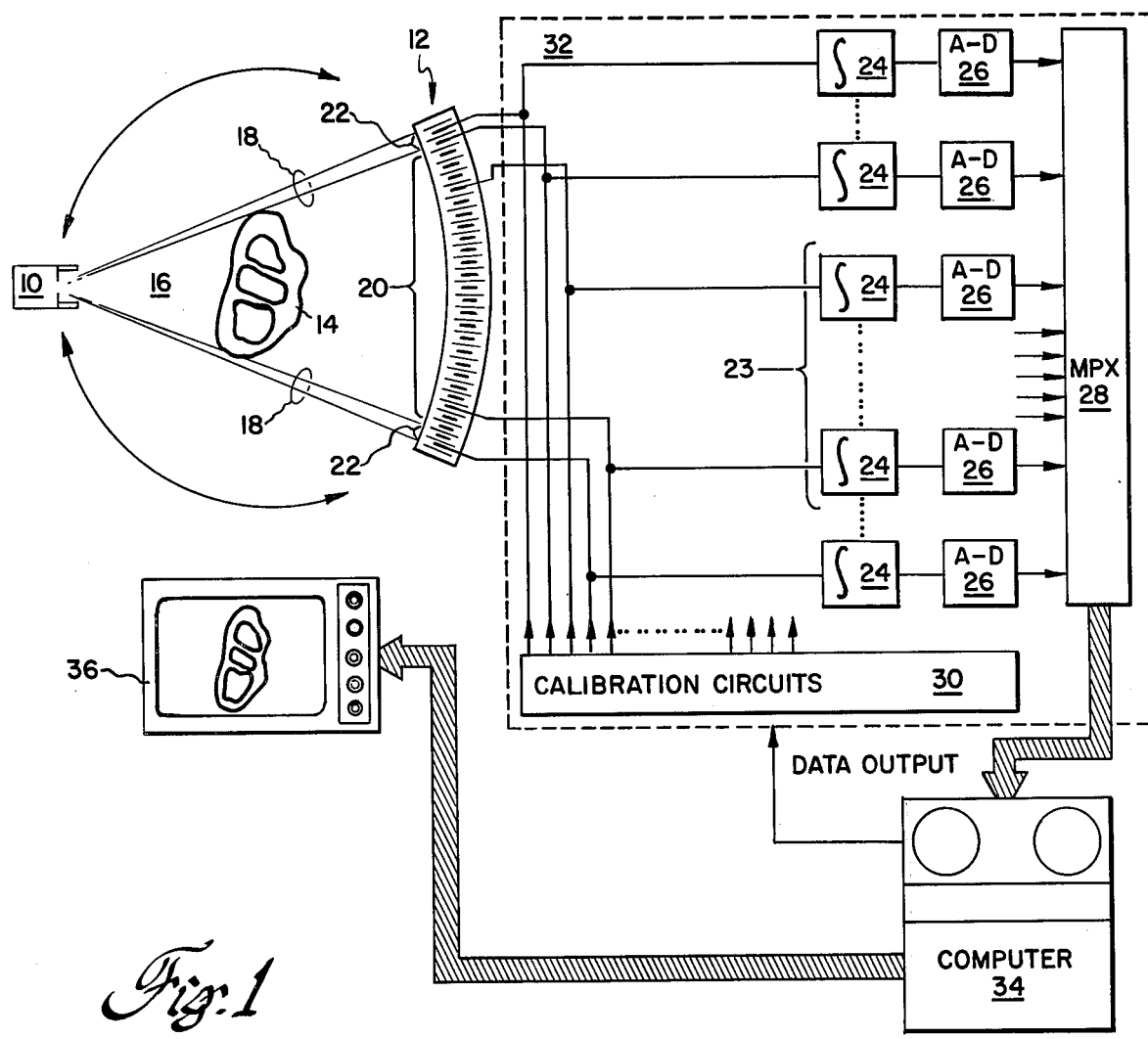
FIG. 1 is an x-ray tomographic system which comprises a data acquisition system of the present invention.

FIG. 1 is a computerized transverse axial tomography system of the present invention. A body 14 undergoing examination is interposed between a pulsed x-ray source 10 and an array of x-ray detectors 12. In a typical system, the x-ray detector array 12 may, for example, comprise an array of ionization chamber cells filled with xenon gas at a pressure between approximately 10 atmospheres and approximately 100 atmospheres. The x-ray source 10 typically includes collimation means which function to confine the x-ray energy emanating from the source into a substantially planar, sectorial beam. A central sector of the x-ray beam 16 illuminates the body 14 and is transmitted through the body to a group of ionization chamber cells 20 in the center of the array 12. The angle of the x-ray beam is larger than the angle subtended by the body 14 so that two peripheral sectors of the beam 18 are transmitted past the body, without substantial attenuation, to groups of ionization chamber cells 22 at the periphery of the array 12. In a typical array, the central group 20 may, for example, comprise 289 separate ionization chamber cells while each of the peripheral reference detector groups 22 may comprise six independent ionization chamber cell groups.

Signals from each of the ionization chamber cells in the central group 20 flow into separate data acquisition channels 23 where they are integrated, measured, and converted to a digital format for transmission to a digital computer 34. Signals from groups of detector cells in the peripheral portions 22 of the array are likewise directed into data channels for integration, measurement, and analog-to-digital conversion. The peripheral detector channels are utilized, in a method more particularly described below, to compensate the data signals produced by the central cells 20 for variations in the intensity of the x-ray source 10.

The x-ray source 10, the detector array 12, and, typically, the various electronic components in the data collection system 32: that is, integrators 24, analog-to-digital converters 26, a multiplexer 28, and calibration circuits 30, rotate in a plane which passes through the body 14 and thus provide x-ray transmission data for projections along a plurality of intersecting ray paths. Data which is obtained from measurements of x-ray transmission along the ray paths is processed in a digital computer 34, using for example algorithms well known to the art, to produce cross-section images of structures in the body 14. The images may be displayed, for example, on a cathode ray tube monitor 36 which is driven from a digital-to-analog converter associated with the computer 34.

Each data channel 23 comprises circuits for amplifying and integrating the current flow, from one or more ionization chamber cells, during an x-ray pulse. The integrated current, which is proportional to the x-ray flux detected by those ionization chamber cells, is converted to a digital format, typically with an accuracy of at least one part in $2^{14}$ or more, and is transmitted to the digital computer. Data transmission to the digital computer is facilitated by a multiplex circuit 28 which sequentially interrogates and transmits a digital signal from each data channel 23. Timing and control pulses, which are necessary to coordinate the calibration, integration, and analog-to-digital conversion processes, as well as commands for the multiplexer 28 and the calibration circuits 30 are generated within the digital computer 34 and are transmitted to those circuits. The rotation and positioning of the x-ray source 10 and detector array 12 may likewise be controlled by the digital computer or, alternately, may be controlled by a separate microprocessor acting in conjunction with the digital computer.

Figure 2:
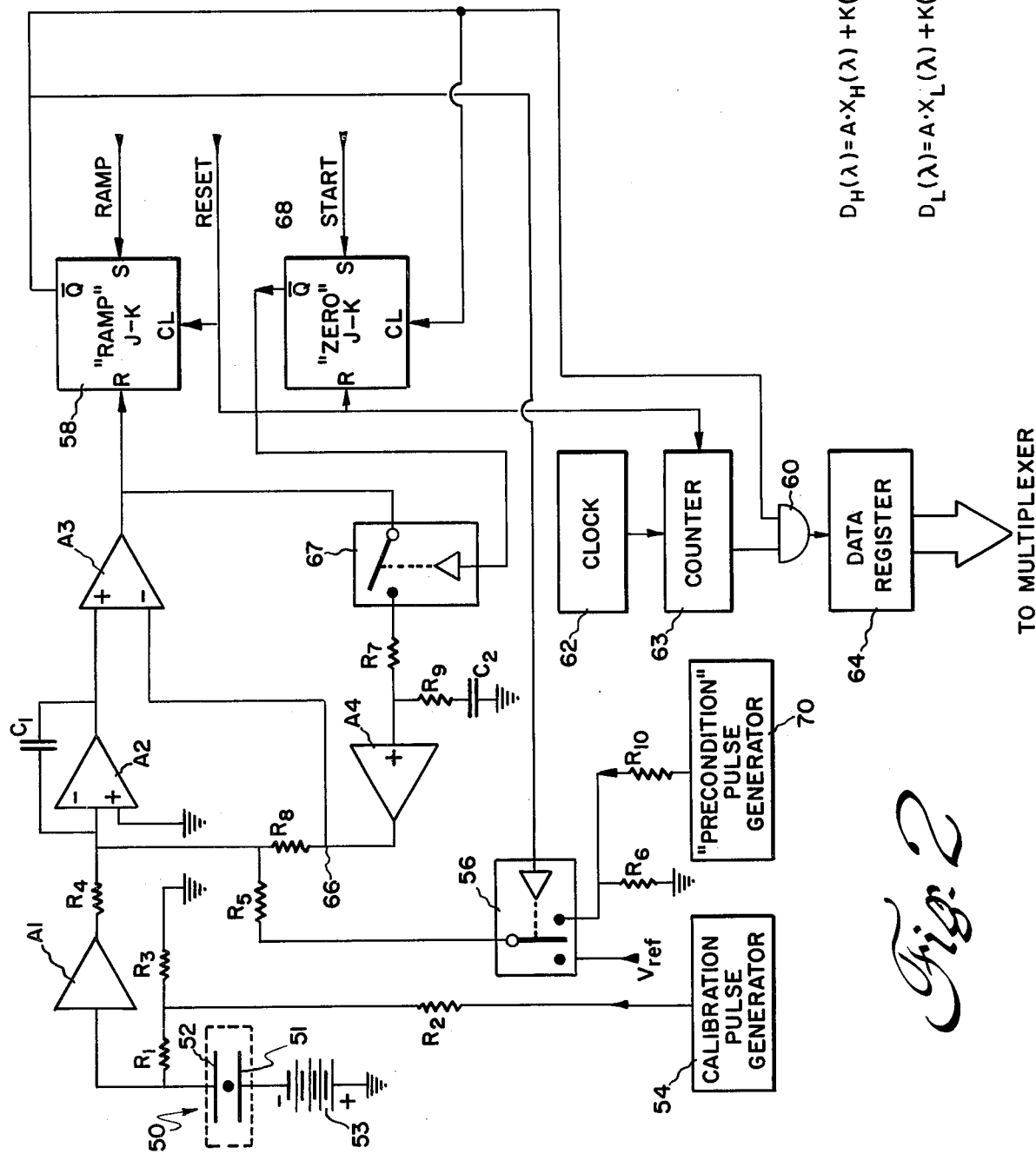
FIG. 2 is a single channel of the data acquisition system of FIG. 1.
Figure 3A:
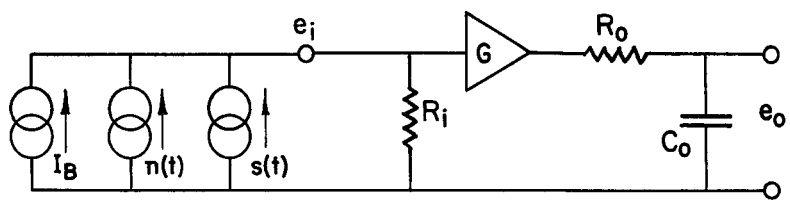
FIGS. 3A and 3B indicate the operation of a comparator amplifier in FIG. 2.
Figure 3B:
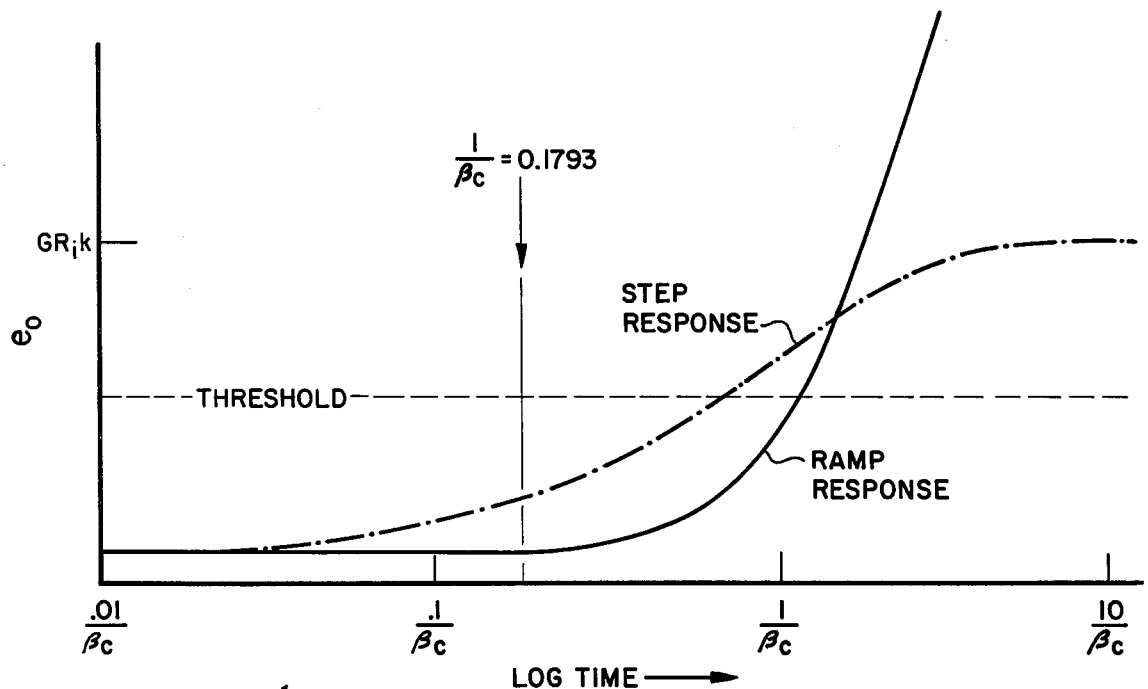

FIG. 2 is a simplified schematic diagram of the electronic components associated with a single data channel 23. An ionization chamber cell 50 comprises a cathode 51 which is disposed opposite an anode 52 in a high pressure detector gas. The cathode 51 is maintained at a negative voltage, with respect to ground, by a voltage source 53. Current from the anode 52 flows through a load resistor $R_1$ to ground. The voltage drop across the load resistor $R_1$ is applied to the input of a power preamplifier $A_1$ which has an extremely high input impedance. The ionization chamber cell 50 is, essentially, a constant current source; the gain of the preamplifier stage $A_1$ is, therefore, effectively proportional to the value of the load resistor $R_1$. In a typical detector channel, the load resistor $R_1$ may, for example, have a resistance of approximately 1 megohm. A calibration resistor $R_3$ is connected in series between $R_1$ and ground. Typically, the resistance of $R_3$ is much less than the resistance of $R_1$. A calibration pulse generator 54 is connected to inject a set of constant voltage, variable width pulses across the resistor $R_3$. A series resistor $R_2$ forms a voltage divider at the calibration pulse generator output. The calibration pulse generator circuit provides a means (more particularly described below) by which the electronic gain and the offset voltage of each data channel 23 may be measured without the use of an x-ray source. This measurement may be performed at the end of each x-ray scan so that electronic drift may be continually monitored and accounted for in the image generation programs.

The accuracy with which the individual data channels can be calibrated against each other depends on the individual voltage divider resistors $R_2$ and $R_3$. These must be accurate and highly stable. Typically, the temperature coefficient of the resistors $R_2$ and $R_3$ is less than or equal to $\pm 25$ ppm/°C.

The preamplifier $A_1$ may be, for example, a wide bandwith, low noise, utility amplifier with an extremely high input impedance and is connected as a voltage follower. The preamplifier thus functions as a power amplifier to transfer the voltage at its high impedance input port to a very low impedance at its output.

The output of amplifier $A_1$ is applied through a resistor $R_4$ to the inverting input of the second amplifier $A_2$. An integrating capacitor $C_1$ is connected as a feedback element between the output and the inverting input of the amplifier $A_2$. The amplifier $A_2$ thus serves to integrate the current flow from the ionization chamber 50 and also functions as part of the analog-to-digital converter circuit 26 (FIG. 1).

The integrator amplifier $A_2$ functions as a dual-slope, analog-to-digital converter. A resistor $R_5$ is connected between the inverting input of amplifier $A_2$ and a CMOS switch 56. The switch 56, which operates under the control of a flip-flop circuit 58, selects a voltage which is applied to the amplifier $A_2$ through resistor $R_5$. During the integration of the x-ray pulse, resistor $R_5$ is connected to ground through resistor $R_6$. Following the integration, a RAMP signal, which is applied to the SET input of flip-flop 58, actuates the switch 56 to apply a reference voltage $V_{ref}$ to resistor $R_5$ and amplifier $A_2$. The output of the flip-flop 58 also controls a gate 60 between a constant frequency counter circuit 63 and a data register 64. The input ports of a comparator amplifier $A_3$ are connected between the output of the amplifier $A_2$ and a virtual ground point 66. The output of the compartor amplifier $A_3$ is connected to a RESET input of the flip-flop circuit 58.

During the x-ray pulse, current from the ionization chamber is integrated on the capacitor $C_1$ to produce a negative voltage at the output of amplifier $A_2$. After the termination of the x-ray pulse, a RAMP signal is applied to the flip-flop 58 switching the $\overline{Q}$ output of the flip-flop to an ON state and actuating switch 56 to apply the voltage $V_{ref}$ to the input of amplifier $A_2$. The voltage $V_{ref}$ is integrated on the capacitor $C_1$ to produce a positive-going voltage at the output of the amplifier $A_2$. As the integrated voltage at the output of amplifier $A_2$ passes through ground potential, the output of the comparator amplifier $A_3$ changes polarity, resets the flip-flop 58, and thus gates the contents of the counter 63 into the data register 64. The count gated into the data register 64 is a measure of the time required to integrate the x-ray data voltage stored on capacitor $C_1$ and is, therefore, a measure of the voltage. The principles of operation of integrating analog digital converters are, of course, well known to the art.

The timing signals which control the individual components of the data acquisition system are generated in a conventional circuit (not shown) in accordance with the operating sequences described below.

THE INTEGRATOR ZEROING CIRCUIT

The comparator amplifier $A_3$ also functions to stabilize and control the dc offset of the analog-to-digital converter. This function is accomplished in a ZERO interval which follows the termination of an analog-to-digital conversion and precedes the initiation of a next x-ray pulse measurement. During this interval, a second CMOS switch 67 closes a negative feedback loop between the output of the comparator amplifier $A_3$ and the input of integrator amplifier $A_2$. The switch 67 connects the output of the comparator amplifier $A_3$ through a resistor $R_7$ to the input of a feedback amplifier $A_4$. The output of amplifier $A_4$, which is the virtual ground node 66, is connected to the inverting input of amplifier $A_2$ through a resistor $R_8$. An RC holding circuit comprising a resistor $R_9$ and a capacitor $C_2$ is connected from the input of the amplifier $A_4$ to ground and functions to minimize the effects of circuit noise and to hold voltage-zero information during the integration and conversion portions of the circuit operating sequence. The CMOS switch 67 is open during those portions of the sequence. The feedback amplifier $A_4$ is utilized as a unity gain buffer to prevent loading of the holding capacitor $C_2$ during the integration and conversion portions of the operating sequence when the CMOS switch 67 is open.

Figure 3:
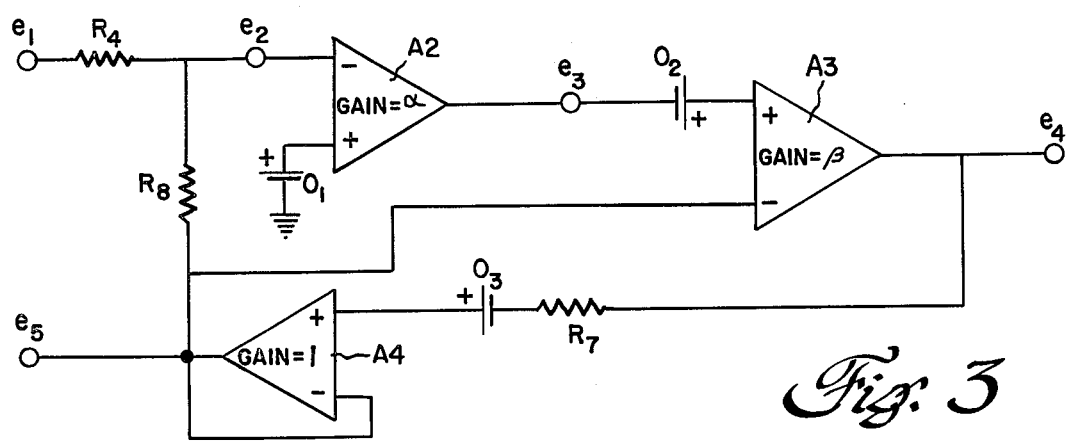
FIG. 3 indicates the operation of a feedback loop in the integrator circuit of FIG. 2.

The operation of the zeroing circuit is described with reference to FIGS. 2 and 3 wherein:

$e_1$ is the dc output voltage of the preamplifier $A_1$ with no signal from the ionization chamber 50; it includes all preamplifier offsets;

$e_2-e_5$ are the dc voltage levels determined by the zeroing circuit;

$o_1$ is the offset voltage of the integrator amplifier $A_2$;

$o_2$ is the offset voltage of the comparator amplifier $A_3$; and $o_3$ is the offset voltage of the feedback amplifier $A_4$.

The approximate formulae for the dc operating levels of the zeroing circuit are:

$$e_2 \approx e_1\left(\frac{R_8}{\alpha R_4}\right) + o_1 + o_2\left(\frac{1}{\alpha}\right) + o_3\left(\frac{1}{\alpha\beta}\right) \quad (1)$$

$$e_3 \approx e_1\left(-\frac{R_8}{R_4}\right) + o_1\left(\frac{R_4+R_8}{R_4}\right) - o_2 - o_3\left(\frac{1}{\beta}\right) \quad (2)$$

$$e_4 \approx e_1\left(-\frac{R_8}{R_4}\right) + o_1\left(\frac{R_4+R_8}{R_4}\right) + o_2\left(\frac{R_4+R_8}{\alpha R_4}\right) - o_3 \quad (3)$$

$$e_5 \approx e_1\left(-\frac{R_8}{R_4}\right) + o_1\left(\frac{R_8+R_4}{R_4}\right) + o_2\left(\frac{R_4+R_8}{\alpha R_4}\right) + o_3\left(\frac{R_4+R_8}{\alpha\beta R_4}\right) \quad (4)$$

$$(e_3-e_5) \approx e_1\left(\frac{R_4}{\beta R_8}\right) + o_1\left(\frac{R_4+R_8}{\beta R_4}\right) - o_2 - o_3\left(\frac{1}{\beta}\right) \quad (5)$$

The voltage difference $(e_3-e_5)$ between the two input ports of the comparator amplifier $A_3$ during the zeroing interval is the voltge from which the x-ray and preamplifier-integrator output is measured. This voltage $(e_3-e_5)$ should ideally be equal to $(-o_2)$ in order to compensate for the offset $(+o_2)$ of the comparator amplifier $A_3$. Formula 5 shows that this condition is closely met if the gain of the comparator $A_3$ is very large. (As an example, if the full scale integrator voltage on capacitors $C_1$ is approximately 1.5 volts and the resolution of the analog-to-digital converter 14 bits, the bit resolution is approximately 100 microvolts; if the residual offset error of the zero system is limited to 50 microvolts ($\frac{1}{2}$ bit), $R_4 = 15.3$ kilohms, $R_7 = 1$ kilohm, $R_8 = 51$ kilohms, and the amplifier offsets $o_1$ and $o_3$ are 20 millivolts, the required gain of the comparator amplifier $A_3$ is at least 70 dB.)

The zeroing circuit control switch 67 is actuated by the $\overline{Q}$ output of a second JK flip-flop 68. The flip-flop 68 receives RESET and START signals which close the zeroing circuit switch 67 at the end of an analog-to-digital conversion cycle and then open the switch before the next x-ray pulse is started. The RESET function also serves to zero the data counter 63 after its contents are transferred to the digital computer.

The zeroing circuit, thus, functions to effectively establish a zero current at node $e_2$ when the voltage at node $e_1$ is held at a fixed value. The circuit will, therefore within limits, compensate for a fixed background signal from the x-ray detector.

The methods and circuits for compensating offset voltages have been described with reference to a single-slope, analog-to-digital converter with an integrating input stage. Those skilled in the art will recognize, however, that the principles are, generally, equally applicable to dual-slop and successive approximation converters or to any other type of analog signal processing circuits which comprise one or more comparator elements.

However, the offset voltage compensating circuit described herein is particularly suited for use in combination with ramp-type, analog-to-digital converters. It will, of course, be recognized that the output voltage of the converter circuit, during the zeroing process will include an additive noise component which is proportional to the bandwidth of the feedback circuit. A narrow band feedback circuit is, therefore, desirable from the standpoint of reducing conversion errors which are attributable to random noise. The settling time of the zeroing circuit is, however, inversely proportional to its bandwidth to that of the actual bandwidth, as determined by the values of $C_2$ and the associated resistances, and will necessarily be a compromise which assures a reasonable settling time and an acceptable noise level.

The combination of a single-slope or dual slope converter with the zeroing feedback loop assures that the signal voltages on the converter components will be nearly zero at the end of a conversion interval and that the voltage changes introduced in the subsequent zeroing process will be significantly smaller than those which would be necessary to zero a converter which produced non-zero signal voltages at the end of the conversion interval; for example, a ramped reference analog-to-digital converter.

The smaller voltage excursions which are produced when a single-slope or dual-slope converter is used with the zeroing feedback loop permit the use of a narrower feedback bandwidth than would be possible with another converter type and thus function to reduce circuit noise.

The amplifier $A_3$ must function both as a high speed comparator and a fast, high frequency operational amplifier. It is, however, extremely difficult to make conventional "comparator" integrated circuits act as stable amplifiers. The same comparator unit must be included in the analog-to-digital converter and in the zeroing feedback circuit so that the offset voltage of an individual comparator may be properly cancelled. This results in a dual requirement which fast integrated circuit comparators cannot meet.

A high frequency, fast response operational amplifier may be utilized as the comparator element $A_3$ in the circuit of FIG. 2. The action of such an amplifier in a single-slope or dual-slope, analog-to-digital converter tends to limit the effective noise bandwidth of the amplifier in a more effective manner than would other types of converter circuits (i.e., single-slope or successive approximation circuits).

The variable signal which is applied to the input of the comparator in these circuits is a ramp function whereas the input to the comparator of other converter circuits is, generally, a series of step functions. Ramp-type converter circuits of this type are generally more immune to noise than are step-type circuits with the same comparator bandwidth.

THE INTEGRATOR PRECONDITIONING CIRCUIT

High frequency, fast response integrated circuit operational amplifiers may be utilized as voltage comparators. However, such integrated circuits may exhibit propagation delays of as much as 10 microseconds. Those propagation delays, if not properly compensated, can introduce substantial offsets into an analog-to-digital conversion process.

In accordance with the present invention, a calibrated "preconditioning" pulse is integrated immediately before each x-ray measurement. The preconditioning circuits comprise a constant-area pulse generator 70 which is connected through a resistor $R_{10}$ to the node of resistor $R_6$ and the CMOS reference voltage switch 56. During a preconditioning interval, switch 56 connects the pulse generator 70 to the input of the integrator amplifier $A_2$ through resistor $R_5$.

The operation of the integrator, the analog-to-digital converter, and the preconditioning circuits are illustrated with reference to FIGS. 4A-4I, which are circuit waveforms during a single x-ray measurement sequence. The measurement sequence may, for ease of description, be divided into four intervals: a PRECONDITION interval of approximately $3 \times 10^{-4}$ seconds; an INTEGRATION interval of approximately $5 \times 10^{-3}$ seconds following the PRECONDITION interval, a CONVERSION interval of approximately $5 \times 10^{-3}$ seconds; and a ZERO interval of approximately $5 \times 10^{-3}$ seconds. The horizontal scales of FIGS. 4A-4I have been distorted to clarify events which occur during these intervals.

Prior to the start of the PRECONDITION interval, all the amplifier input and output voltages are zero (assuming zero offset voltage). Resistor $R_5$ is connected by switch 56 to the voltage divider resistors $R_6$ and $R_{10}$. The output of the pulse generator 70 is zero. Switch 67 is closed and the zeroing feedback loop circuit is active.

A START pulse (FIG. 4B) is applied to the SET input of the zeroing control flip-flop 68 during the PRECONDITION interval. The START pulse sets the flip-flop 68 and thus opens switch 67, forcing the circuit into an integrating state. No integration occurs, however, because all signal inputs are zero. The START pulse must last for the full PRECONDITION interval, for reasons explained below.

Shortly after the occurrence of the leading edge of the START pulse, a positive PRECONDITION pulse (FIG. 4C) is applied through resistor $R_{10}$ by the pulse generator 70. After being attenuated in the voltage divider $R_{10}$ and $R_6$, the PRECONDITION pulse is applied to the integrator amplifier $A_2$ input via the switch 56 and the resistor $R_5$. The PRECONDITION pulse input causes the amplifier $A_2$ to integrate, generating a small negative output 100 (FIG. 4F) which drives the comparator amplifier $A_3$ to negative saturation 101 (FIG. 4G).

After the PRECONDITION pulse has terminated, a RAMP pulse 102 is generated (FIG. 4D) which sets the flip-flop 58 and connects the integrator amplifier $A_2$ input to the negative reference voltage $V_{ref}$ through resistor $R_5$ and switch 56. The amplifier $A_2$ integrates the reference voltage to produce a highly linear, positive slope ramp voltage at its output (starting at a negative voltage 100 and proceeding towards zero volts 103 (FIG. 4F)).

As the integrator output (FIG. 4F) goes through zero volts, the comparator $A_3$ starts to switch. However, there is a delay $\Delta$ in the comparator amplifier $A_3$. The RAMP 103 continues positive to a value 104 which is proportional to this delay $\Delta$. When the comparator does switch (FIG. 4G), the integrator output is a positive voltage 104 where it will remain until the actual x-ray integration begins.

When the comparator $A_3$ switches, it resets the flip-flop 58 disconnecting the reference voltage. It will not, however, reactivate the zeroing switch 67 because the START pulse is still present and thus overrides the other inputs of the flip-flop 68. The circuit, therefore, remains in the offset state described above.

After a short delay, the INTEGRATION period commences. During this period, the amplified X-RAY detector signal (FIG. 4E) is applied to the input of amplifier $A_2$. The signal is integrated during this period by amplifier $A_2$, capacitor $C_1$, and resistor $R_4$ so that the output of amplifier $A_2$, $E_i$, is $$E_i = \frac{-1}{R_4 C_1} \int_0^t E_p dt \qquad (6)$$

where $E_p$ is the output of the preamplifier $A_1$.

At the end of the INTEGRATION period, the input voltage at the preamplifier $A_1$ is substantially zero and the output voltage of amplifier $A_2$ is some negative value 105. A RAMP input 106 (FIG. 4D) is then applied to the SET input of the flip-flop 58 actuating switch 56 to connect resistor $R_5$ to the reference voltage. The circuit is now in the analog-to-digital CONVERSION interval. The amplifier $A_2$ integrates the reference voltage $V_{ref}$ to produce a highly liner, positive slope ramp 107 (FIG. 4F), starting at a negative voltage and proceeding towards zero volts during a time interval which is precisely proportional to the magnitude of the initial negative voltage:

$$t = \frac{R_5 C_1}{V_{Ref}} E_1 \qquad (7)$$

The time interval is measured by the data register 64, counter 63, and clock 62.

During the conversion, the integrator output (solid line of FIG. 4F) will pass through zero slightly sooner than it normally would (dashed curve of FIG. 4F). The difference is timing $\Delta$ is equal to the delay of the comparator. After this time delay, the comparator $A_3$ output resets the flip-flop 58 which feeds a $\overline{Q}$ timing signal to the data register gate 60 and simultaneously disconnects the reference voltage, thus stopping the conversion. The difference in timing, attributable to the residue from the integration of the PRECONDITION pulse, is equal to the delay $\Delta$ in the comparator amplifier $A_3$; thus, when the comparator does switch after its delay, the timing pulse to the data register gate occurs at the correct time.

The $\overline{Q}$ output of the flip-flop 58 is also applied to a CLOCK input of flip-flop 68 and thus initiates zeroing of the integrator via the switch 67. The circuit is now in a stable zero state where it will remain until the next START pulse.

If, due to an excessive x-ray input, the conversion ramp has not crossed zero volts during the alloted conversion time, a RESET input 108 (FIG. 4A) resets the flip-flop 58, terminating the conversion. This action is accompanied by the loading of an overrange bit into the data register 64. A RESET input will also initiate integrator zeroing.

The preconditioning circuit operation, described above, produces a dead-band at very low signal levels. The conversion circuit will treat all positive integrator outputs as zero; that is, the output of the x-ray detector must have sufficient amplitude to drive the integrator negative during the INTEGRATION period, otherwise the digital output will equal zero. Thus, for example, if the clock period is approximately 300 nanoseconds, the comparator delay $\Delta$ is approximately 10 microseconds, the dead-band is approximately 33 counts, and the full scale range of the register is approximately 16,000 counts, the dynamic range of the conversion is limited to the range between 10 microseconds and 5 milliseconds with a resolution of 0.3 microseconds.

Other modes of circuit operation are possible to eliminate the low range, dead-band characteristic of the preconditioning circuit. (1) Normal integration without a preconditioning ramp: the digital output of each channel will have an offset, but will not exhibit a dead-band. (2) Operation with a preconditioning pulse, a preconditioning ramp, and a second preconditioning pulse: a calibrated offset will be applied to the system, the value of the offset being equal to the integration of the second preconditioning pulse. There is no dead-band, however, since the second preconditioning pulse will drive the integrator output negative. The prepulse generator must be an accurate, stable circuit to allow this mode of operation. (3) Operation with a single preconditioning pulse and no preconditioning ramp: a single preconditioning pulse may be used to prebias the single processing circuit and, thus, eliminate a dead-band.

Under large signal conditions, some x-ray detectors (i.e., ionization chambers) may produce output signals having low level tails which continue after the end of the x-ray pulse. The converter circuit of the present invention permits some signal output during the CONVERSION interval which allows for "clean-up" of these residual signal components. The time required for the actual conversion is proportional to the signal level in converters of this type so that the integration period for high level signals is, in effect, extended to allow complete integration of the pulse tail.

AUTOMATIC CALIBRATION SYSTEM

The x-ray source 10 and the x-ray detector array 12 of FIG. 1 typically rotate incrementally around an axis passing through the body 14. The x-ray source is pulsed after each incremental rotation to measure x-ray transmission characteristics of the body along a set diverging ray paths lying within the x-ray beam 16. If, for example, there are approximately 300 detectors in the array 12 and approximately 300 incremental steps in each rotation, approximately 90,000 x-ray transmission data values are measured. This is the basic data from which tomographic images are generated by the computer 34.

These measurements require the maintenance of highly stable (e.g., approximately 1 part in 10,000) electronic gain and offset tolerances in each of the data acquisition channels. Such stability cannot be obtained with state-of-the art electronics. Further, differential changes between the gain or dc offset of the x-ray detector cell, integrator, or analog-to-digital converter in any of the parallel data acquisition channels can introduce serious measurement errors. An automatic calibration system allows continuous measurement of the gain and offset of each data acquisition channel and, thus, permits the rapid and continuous calculation of correction factors which may be applied to the raw data in the digital computer 34.

In the following discussion and claims, the symbols used to represent system parameters are defined in Table I.

TABLE I

| | DEFINITION OF DAS PARAMETERS |
|---|---|
| $\lambda$ | = An ordering number associated with each data acquisition channel which is connected to an x-ray detector cell in center of the array 20 (FIG. 1); |
| R | = An ordering number associated with each data acquisition channel connected to reference x-ray detector cells at the edges of the array 22; |
| $A(\lambda)$ | = The electronic gain of channel $\lambda$ |
| $K(\lambda)$ | = The dc offset of channel $\lambda$ |
| $D(\lambda)$ | = The digital output of channel $\lambda$ |
| $Z(\lambda)$ | = The gain of the x-ray detector cell connected to channel $\lambda$ |
| $X(\lambda)$ | = The output signal from the x-ray detector cell connected to channel $\lambda$ |
| I | = The x-ray source intensity during a measurement; |
| $T_{80}$ | = The absolute transmissivity of the x-ray path measured by channel $\lambda$ |
| $t_\lambda$ | = The relative transmissivity of the x-ray path measured by channel $\lambda$ (transmissivity of water = 1); |
| $C(\lambda)$ | = The digital output of channel $\lambda$ produced by a calibration measurement; |
| $C(R)$ | = The digital output of channel R produced by a calibration measurement; |
| $I'$ | = The x-ray source intensity during a calibration measurement; |
| $A'(\lambda)$ | = The gain of channel $\lambda$ during a calibration measurement; |
| $K'(\lambda)$ | = The dc offset of channel $\lambda$ during a |

TABLE I-continued
DEFINITION OF DAS PARAMETERS

| | | |
|---|---|---|
| $C'(\lambda)$ | = | The digital output of a channel $\lambda$ during a calibration measurement corrected for variations in the gain and the offset of the channel; |
| $W_{80}$ | = | The absolute transmissivity of a water calibration standard; |
| $X_L(\lambda)$ | = | The integrated value of a low-level calibration pulse in channel $\lambda$ |
| $X_H(\lambda)$ | = | The integrated value of a high-level calibration pulse in channel $\lambda$ |
| $D_L(\lambda)$ | = | The digital output of channel $\lambda$ produced by a pulse $X_L(\lambda)$ |
| $D_H(\lambda)$ | = | The digital output of channel $\lambda$ produced by a pulse $X_H(\lambda)$ |

The transfer function of each data acquisition channel may be described as:

$$D(\lambda) = A(\lambda)X + K(\lambda) \qquad (8)$$

Figure 5:
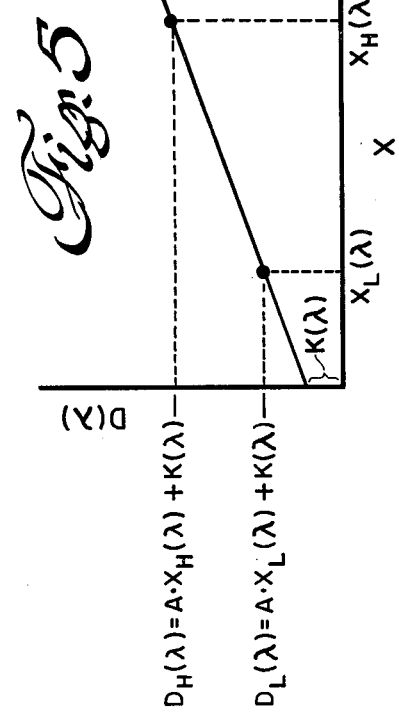
FIG. 5 is the transfer function of a data acquisition channel.

To account for the potential drifts in $A(\lambda)$ and $K(\lambda)$, two electronic calibration signals, having values $X_L(\lambda)$ and $X_H(\lambda)$, respectively, are injected into each data acquisition channel by the calibration pulse generator 54 (FIG. 2). Most advantageously, the calibration pulses have equal amplitudes and have widths which are adjusted to give them different integrated values. The transfer function of a typical data channel and its response to the calibration signals are illustrated in FIG. 5. For each calibration measurement in each data channel $\lambda$, it can be determined that $$A(\lambda) = \frac{D_H(\lambda) - D_L(\lambda)}{X_H - X_L} \qquad (9)$$

and $$K(\lambda) + D_H(\lambda) - A(\lambda)X_H \qquad (10)$$

The calibration data $D_L(\lambda)$ and $D_H(\lambda)$ is used to correct the x-ray data $D(\lambda)$ for any electronic drift which has occurred since the last periodic system calibration.

During a periodic system calibration, the computerized tomography system scans a phantom having known x-ray transmission characteristics. Either air or water phantoms may be used for these measurements but, for ease or description, a water phantom will be assumed. During the periodic system calibration, the output of the channels connected to the measurement detector cells 20 and to the reference detector cells 22 are, respectively, $$C(\lambda) = Z(\lambda)A'(\lambda)W_\lambda I' + K_\lambda' \qquad (11)$$

$$C(R) = Z(R)A'(R)I' + K_R' \qquad (12)$$

During a subsequent body scan those channel outputs are, respectively, $$D(\lambda) = Z(\lambda)A(\lambda)T_\lambda I + K(\lambda) \qquad (13)$$

$$D(R) = Z(R)A(R)I + K_R \qquad (14)$$

The values of $A'(\lambda)$ and $A'(R)$ will, because of electronic drift, normally differ from the values of $A(\lambda)$ and $A(R)$.

The inputs to the image reconstruction programs in the digital computer are the natural logarithm of the relative x-ray transmissivites; that is:

$$Lnt_\lambda = Lnt'_\lambda - LnW_\lambda \qquad (15)$$

Combining equations (11)–(15), it may be seen that $$Ln \, t_\lambda = Ln \, \{D(\lambda) - K(\lambda)\} - Ln \, \{C(\lambda) - K'(\lambda)\} \qquad (16)$$
$$+ Ln\left(\frac{C(R) - K(R)}{D(R) - K(R)}\right) + Ln\left(\frac{A(R)A'(\lambda)}{A'(R)A(\lambda)}\right)$$

The third term in equation 16 corrects the raw data for changes in the x-ray source intensity while the fourth term corrects the raw data for drift in the electronics of the data acquisition system.

EXAMPLE OF AN AUTOMATIC CALIBRATION PROCEDURE

Figure 6:
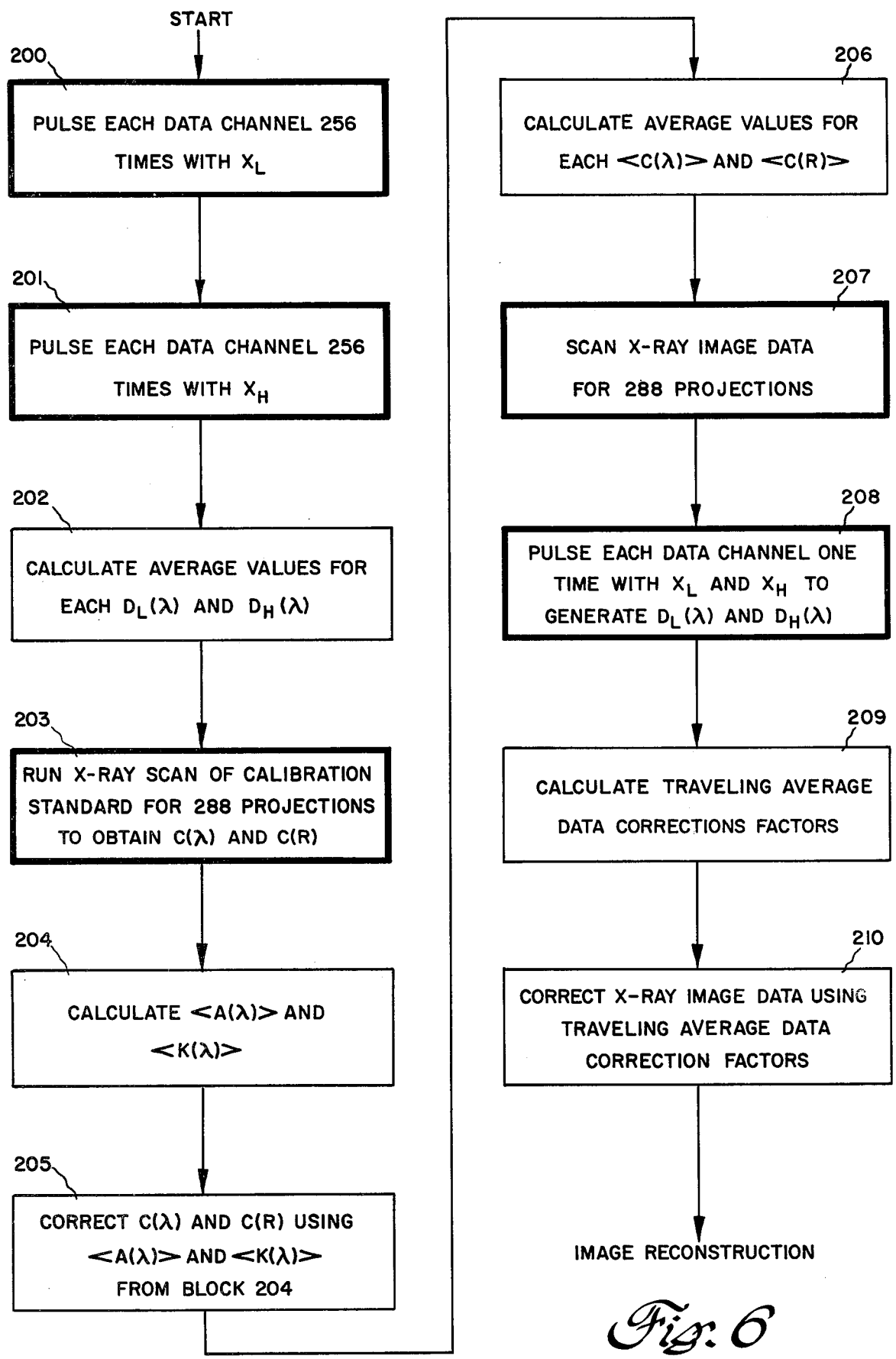
FIG. 6 is a flow chart of automatic calibration methods of the present invention.

The foregoing calibration circuits and data correction equations may, for example, be applied to a computerized x-ray tomography system in a sequence illustrated in FIG. 6.

The average transfer function parameters for each data acquisition channel, $<A(\lambda)>$ and $<K(\lambda)>$, are measured by pulsing each channel two hundred fifty-six times, first with a low-level calibration pulse $X_L$ 200 and then with a high-level calibration pulse $X_H$ 201. The values of the high-level digital output $D_H(\lambda)$ and the low-level digital output $D_L(\lambda)$ from each channel are then averaged in the digital computer in accordance with the equation $$<D(\lambda)> = \frac{1}{256} \sum_{N=0}^{255} D(\lambda)_N \qquad (17)$$

An x-ray scan is then made of a phantom to obtain values of $C(\lambda)$ and $C(R)$ 203. The average values of $D_L(\lambda)$ and $D_H(\lambda)$ obtained in step 202 are then utilized in equations (9) and (10) to calculate average values for $A(\lambda)$ and $K(\lambda)$ 204. $<A(\lambda)>$ and $<K(\lambda)>$ are then used to correct values of $C(\lambda)$ and $C(R)$ obtained from the phantom measurement 205;

$$<A(\lambda)> = \frac{<D_H(\lambda)> - <D_L(\lambda)>}{X_H - X_L} \qquad (18)$$

$$<K(\lambda)> = <D_H(\lambda)> - <A(\lambda)>X_H \qquad (19)$$

$$C'(\lambda) = <A(\lambda)>[C(\lambda) - <K(\lambda)>] \qquad (20)$$

The values for $C(\lambda)$ and $C(R)$ are then averaged over all rotational positions of the source and detector array 206.

X-ray data is then measured on a body 14 (FIG. 1) for each rotational scan position 207. After the scan rotation is completed, each data channel is pulsed one time with high and low level calibration pulses $X_H$ and $X_L$ to generate outputs $D_H(\lambda)$ and $D_L(\lambda)$ 208. A travelling average of the data calibration digital outputs is then calculated 209 from the equations $$<D_L(\lambda)> = \frac{1}{64} D_L(\lambda) + \frac{63}{64} <D_L(\lambda)> \qquad (21)$$

$$<D_H(\lambda)> = \frac{1}{64} D_H(\lambda) + \frac{63}{64} <D_L(\lambda)> \qquad (22)$$

The x-ray scan data obtained in step 207 is then corrected using the travelling average values from step 209 in equations (8), (9), and (16) 210. The output of step 210 represents x-ray transmission data which has been corrected for drift in the gain and dc offset of each data acquisition channel as well as for variation or drifts in the x-ray source intensity.

Tomographic systems comprising the high and low level pulse calibration circuits of the present invention produce high accuracy image data, which is corrected for short term systems drift. The interval between standard phantom calibrations of the tomography equipment is thereby increased over the intervals of the prior art.

While the invention has been described in detail herein in accord with certain preferred embodiments, many modifications and changes therein may be effected by those skilled in the art. Accordingly, it is intended by the appended claims to cover all such modifications and changes as fall within the true spirit and scope of the invention.

The invention claimed is:

1. A method of operating an analog-to-digital converter circuit, which circuit comprises integrating means and comparator means which function to produce a logical signal which changes state in response to the sign of the difference between the value of a reference signal and the value of a signal from the integrating means, the comparator means being further characterized by a significant propagation delay time; the method comprising the steps of sequentially:
  a. integrating a preconditioning signal of a first polarity with said integrating means;
  b. integrating a reference signal of opposite polarity from the voltage level obtained by integrating the preconditioning signal through a reference value until the logical signal changes state, whereby a negative residue signal proportional to the propagation delay is produced on the integrating means;
  c. integrating a data signal and adding the integral of the data signal to the negative residue signal on the integrating means; and
  d. integrating the reference signal of opposite polarity from the sum of the residue signal and the integrated data signal toward the reference value and digitally timing the period from the start of the integration of the sum until a change in the state of the logical signal,
  whereby a digitization of the data signal is produced and offsets attributable to the propagation delay are cancelled.

2. The method of claim 1 wherein the reference value is zero volts.

3. The method of claim 2 wherein the integrating means comprise an operational amplifier and a capacitor and the step of applying a preconditioning signal comprises integrating a pulse of current with the capacitor.

4. The method of claim 2 further comprising the step of periodically connecting feedback means to substantially cancel offset signals at the input to the integrating means.

5. The method of claim 2 wherein:
  a plurality of the analog-to-digital converter circuits are operated in parallel to simultaneously digitize a plurality of data signals;
  the preconditioning signals are applied to all of the analog-to-digital converters from a common source; and
  a single, common clock is utilized for timing the period in all of the analog-to-digital converters.

6. In a ramp-type, analog-to-digital converter circuit of the type comprising integrating means connected to receive and integrate signals, comparator means connected to produce a logical signal in response to the polarity of the difference of an output of the integrating means subtracted from a reference signal, and timing means functioning to produce a digitization of the time period between the start of the integration of the data signal and the occurrence of a value of the logical signal which indicates a change in the polarity of the difference; wherein the comparator means are characterized by a significant propagation delay time between the occurrence of the change of polarity of the difference and the occurrence of the corresponding value of the logical signal, the improvement comprising;
  means for applying a preconditioning signal to the integrating means prior to the reception of a data signal;
  means for causing the integrating means to integrate the preconditioning signal through a reference value until the comparator produces a signal indicating a change of polarity, whereby a negative residue signal is produced on the integrating means;
  means for applying the data signal to said integrating means in the presence of said residue signal;
  means for causing the integrating means to integrate the data and residue signals through the reference value;
  and
  means associated with said timing means for providing a digitization of the data signal without offsets attributable to propagation delays.

7. The circuit of claim 6 wherein the reference value is zero volts.

8. The method of claim 7 wherein the circuit further comprises feedback means which are periodically connected between the output of the comparator means and the input of the integrating means and which function to substantially cancel offset signals at the input of the integrating means.

9. A data acquisition system for a computerized x-ray tomography machine comprising a plurality of the circuits of claim 7 connected to simultaneously process a plurality of data signals;
  wherein the means for applying the preconditioning signals comprise a single pulse generator connected to supply a single preconditioning pulse to all of the converter circuits in parallel; and
  wherein a single, common clock supplies time base signals to the timing means in all of the converter circuits.

10. The circuit of claim 6 wherein the integrating means comprise an operational amplifier and a capacitor and, the means for applying the preconditioning signal are means for integrating a current pulse with the capacitor.

* * * * *